United States Patent
Matsumoto et al.

(10) Patent No.: US 9,442,052 B2
(45) Date of Patent: Sep. 13, 2016

(54) TORSION TESTER

(71) Applicant: KOKUSAI KEISOKUKI KABUSHIKI KAISHA, Tokyo (JP)

(72) Inventors: Sigeru Matsumoto, Tokyo (JP); Hiroshi Miyashita, Tokyo (JP); Kazuhiro Murauchi, Tokyo (JP); Masanobu Hasegawa, Tokyo (JP); Tomotaka Sakagami, Tokyo (JP)

(73) Assignee: Kokusai Keisokuki Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/228,701

(22) Filed: Mar. 28, 2014

(65) Prior Publication Data

US 2014/0208863 A1 Jul. 31, 2014

Related U.S. Application Data

(63) Continuation-in-part of application No. PCT/JP2012/074634, filed on Sep. 26, 2012.

(30) Foreign Application Priority Data

Sep. 30, 2011 (JP) .................. 2011-218789

(51) Int. Cl.
*G01N 3/22* (2006.01)
*G01N 3/02* (2006.01)
*G01M 13/02* (2006.01)
*G01L 3/02* (2006.01)

(52) U.S. Cl.
CPC . *G01N 3/02* (2013.01); *G01L 3/02* (2013.01); *G01M 13/021* (2013.01); *G01M 13/025* (2013.01); *G01N 3/22* (2013.01)

(58) Field of Classification Search
CPC ...... G01L 5/0042; G01L 3/02; G01M 13/02; G01M 13/025; G01M 13/021; G01N 3/22; G01N 3/02
USPC ............. 73/847, 862.324, 862.325, 862, 324
See application file for complete search history.

(56) References Cited

U.S. PATENT DOCUMENTS

| | | | |
|---|---|---|---|
| 3,754,437 A | 8/1973 | Kanbel et al. | |
| 4,468,958 A | 9/1984 | Takeshita | |
| 4,712,052 A * | 12/1987 | Omae et al. ................. | 318/625 |
| 4,989,686 A * | 2/1991 | Miller et al. ................. | 180/197 |
| 6,418,767 B2 * | 7/2002 | Shinbutsu et al. ............ | 72/10.2 |

(Continued)

FOREIGN PATENT DOCUMENTS

| | | |
|---|---|---|
| CN | 1869625 | 11/2006 |
| CN | 101680828 | 3/2010 |

(Continued)

OTHER PUBLICATIONS

International Search Report issued in PCT/JP2012/074634.
International Preliminary Report on Patentability issued in PCT/JP2012/074634 on Apr. 3, 2014.

(Continued)

*Primary Examiner* — Max Noori
(74) *Attorney, Agent, or Firm* — McCarter & English, LLP

(57) ABSTRACT

A torsion tester including a plurality of driving units configured to connect with and rotate three or more input/output shafts of a test body, respectively, and a controller configured to control the plurality of driving units to be driven with one of individually-set rotational frequencies and individually-set torques, respectively.

9 Claims, 6 Drawing Sheets

(56) References Cited

U.S. PATENT DOCUMENTS

2002/0158180 A1* 10/2002 Noell .................. 248/550
2005/0034540 A1   2/2005 Juranitch et al.
2006/0070457 A1   4/2006 De Lair et al.

FOREIGN PATENT DOCUMENTS

| EP | 1 840 551   | 10/2007 |
|----|-------------|---------|
| JP | 03-200043   | 9/1991  |
| JP | 04232441    | 8/1992  |
| JP | 10-142103   | 5/1998  |
| JP | 2000-105171 | 4/2000  |
| JP | 2000-193574 | 7/2000  |
| JP | 2004-286609 | 10/2004 |
| JP | 2006-064668 | 3/2006  |
| JP | 2007-107955 | 4/2007  |
| JP | 2008-267939 | 11/2008 |

OTHER PUBLICATIONS

Extended European Search Report issued in EP Application No. 12834972.7 on Jul. 3, 2015.
Guohua Zeng, "Research on the Method for Measuring Torque of Rotation Axis", New Technology & New Process, Issue 7, pp. 26-27.
Office Action issued in Chinese Application No. 201280053776.9 on Jun. 2, 2015.
Office Action issued in Chinese Application No. 201280053776.9 on Dec. 29, 2015.
Shuo Guan, "Development of Transmission Loading Test of Engineering Vehicles", CMFD, Engineering Technology vol. II, pp. C035-35, Jun. 15, 2011 China.
Ke Chen et al., "Dynamic Simulation Study of Driving Alex Gear Meshing Based on ADAMS", Transactions Shenyang Ligong University, vol. 29, Issue 1, pp. 28-31 China.

* cited by examiner

TORSION TESTER

CROSS-REFERENCE TO RELATED APPLICATION

This is a Continuation-in-Part of International Application No. PCT/JP2012/074634 filed on Sep. 26, 2012, which claims priority from Japanese Patent Application No. 2011-218789 filed on Sep. 30, 2011. The entire disclosure of the prior applications is incorporated herein by reference.

BACKGROUND

1. Technical Field

The following description relates to one or more techniques for a torsion tester configured to evaluate performance of a power transmission device.

2. Related Art

So far, a fatigue test for a power transmission device such as a propeller shaft has been conducted in such a method as to fix an output shaft of a test body (a power transmission device) to a reaction-force disk, and apply a dynamic or static torque (torsional load) to an input shaft of the test body by a torque applying device such as a servo motor.

SUMMARY

When the power transmission device is installed in an automobile and actually used, loads are applied to the input shaft and the output shaft of the power transmission device, respectively, in a state where a power transmission shaft is rotating. However, in the aforementioned known method, since the power transmission shaft is placed in a static state during the test, it is impossible to accurately evaluate performance of the power transmission device under actual usage environment.

Aspects of the present invention are advantageous to present one or more improved techniques, for a torsion tester, which make it possible to resolve the aforementioned problem.

According to aspects of the present invention, a torsion tester is provided, which includes a plurality of driving units configured to connect with and rotate three or more input/output shafts of a test body, respectively, and a controller configured to control the plurality of driving units to be driven with one of individually-set rotational frequencies and individually-set torques, respectively.

According to aspects of the present invention, further provided is a torsion tester that includes a plurality of driving units configured to connect with and rotate three or more input/output shafts of a test body, respectively, each driving unit including a drive shaft configured to connect with one of an input shaft and an output shaft of the test body, a rotation detector configured to detect a rotational frequency of the drive shaft, and a torque sensor configured to detect a torque applied to the drive shaft, and a controller configured to control the plurality of driving units to be driven with one of individually-set rotational frequencies and individually-set torques, respectively.

BRIEF DESCRIPTION OF THE ACCOMPANYING DRAWINGS

DETAILED DESCRIPTION

It is noted that various connections are set forth between elements in the following description. It is noted that these connections in general and, unless specified otherwise, may be direct or indirect and that this specification is not intended to be limiting in this respect. Aspects of the invention may be implemented on circuits (such as application specific integrated circuits) or in computer software as programs storable on computer readable media including but not limited to RAMs, ROMs, flash memories, EEPROMs, CD-media, DVD-media, temporary storage, hard disk drives, floppy drives, permanent storage, and the like.

First Embodiment

Figure 1:
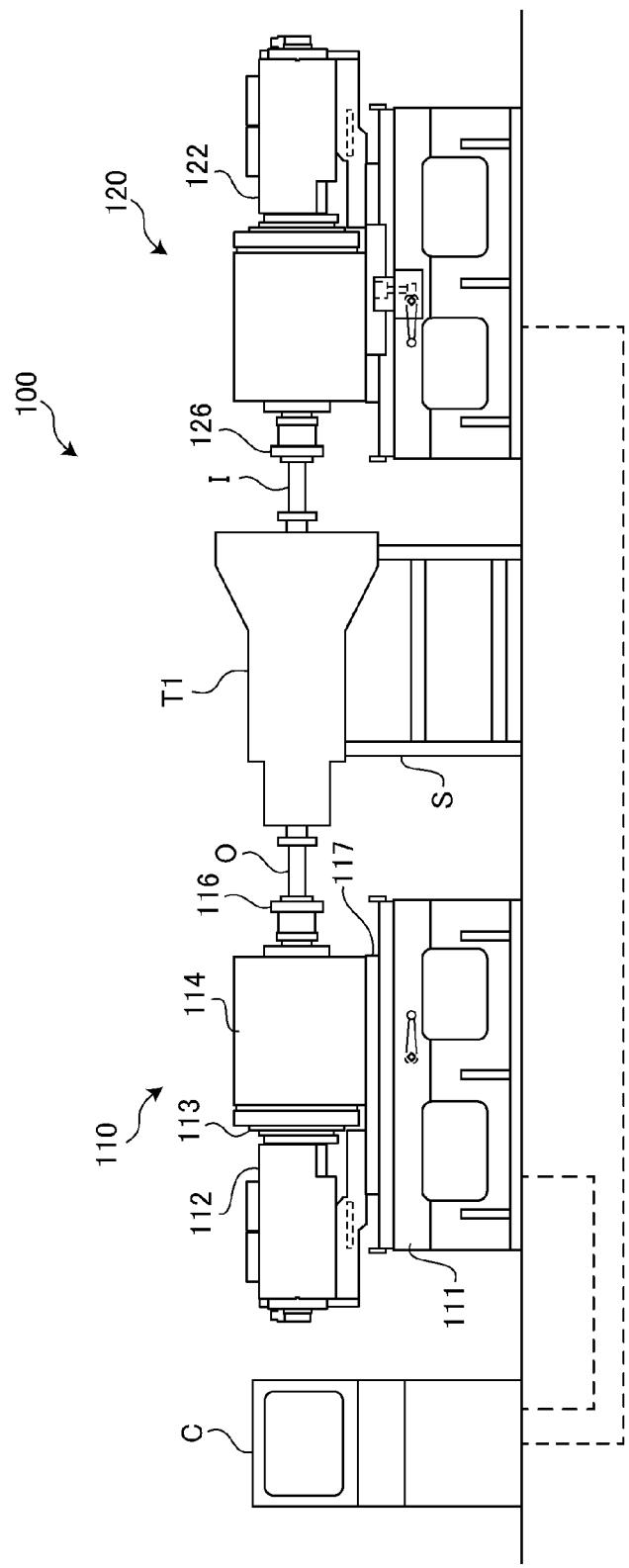
FIG. 1 is a side view of a torsion tester in a first embodiment according to one or more aspects of the present invention.

Hereafter, embodiments according to aspects of the present invention will be described with reference to the accompanying drawings. FIG. 1 is a side view of a torsion tester 100 in a first embodiment according to aspects of the present invention. The torsion tester 100 of the first embodiment is a device for conducting a rotation torsion test for a test body T1 (such as a transmission unit for a rear-wheel drive vehicle) having two rotational shafts. Specifically, the torsion tester 100 is configured to apply a torque to the test body T1 by rotating the two rotational shafts of the test body T1 in synchronization with each other with a phase difference between the rotations of the two rotational shafts. The torsion tester 100 of the first embodiment includes a first driving unit 110, a second driving unit 120, and a controller C configured to take overall control of operations of the torsion tester 100.

Figure 2:
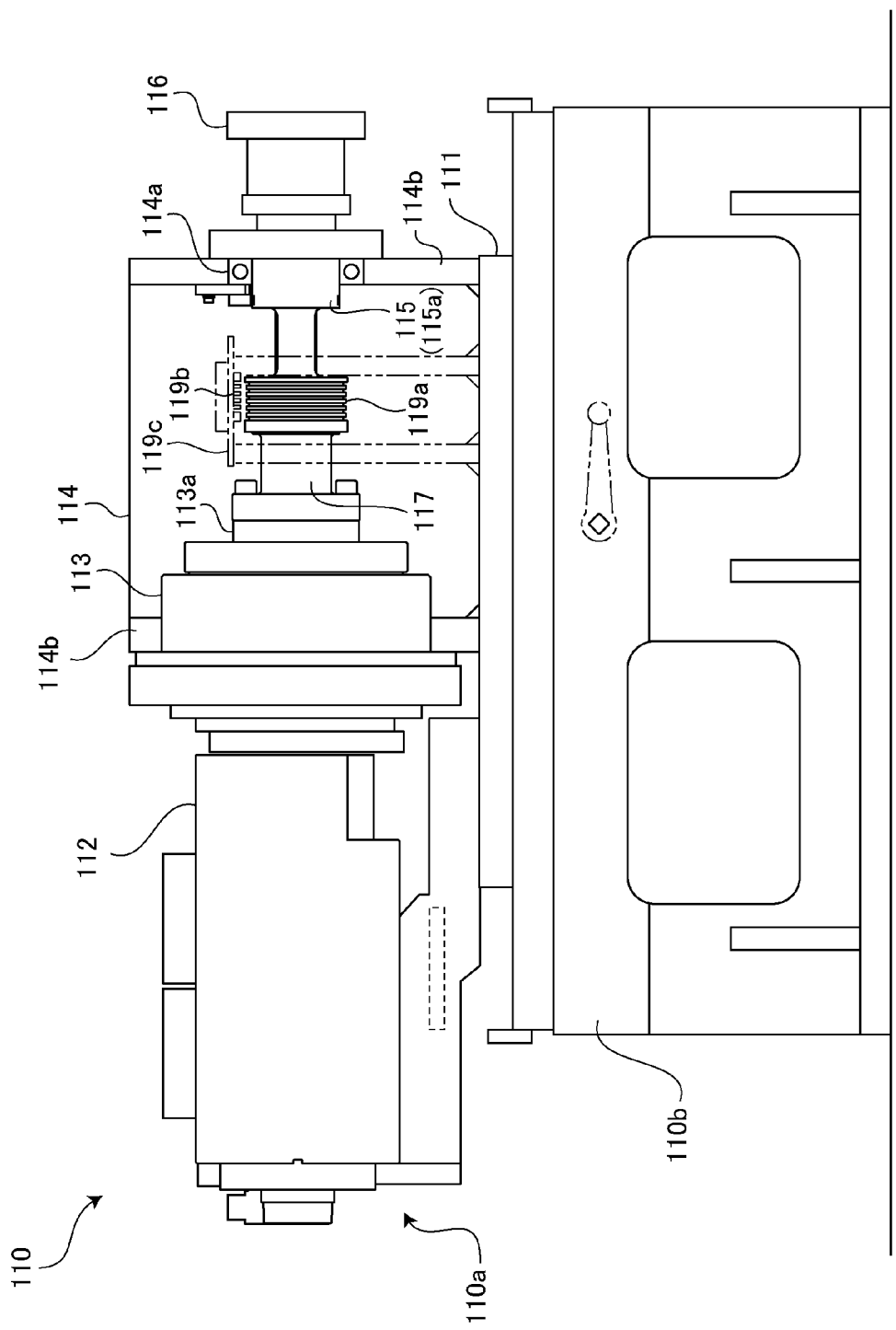
FIG. 2 is a side view of a first driving unit of the torsion tester in the first embodiment according to one or more aspects of the present invention.

First, a configuration of the first driving unit will be described. FIG. 2 is a side view of the first driving unit 110, in which a part is cut off from the first driving unit 110. The first driving unit 110 includes a main body 110a, and a base 110b configured to support the main body 110a at a predetermined height. The main body 110a includes a servo motor 112, a reduction gear 113, a case 114, a spindle 115, a chuck device 116, a torque sensor 117, a plurality of slip rings 119a, and a plurality of brushes 119b. The main body 110a is assembled on a movable plate 111 horizontally disposed on an uppermost portion of the base 110b. The servo motor 112, with an output shaft (not shown) thereof being horizontally directed, is fixed onto the movable plate 111. Further, the movable plate 111 of the base 110b is configured to slide along a direction parallel to the output shaft of the servo motor 112 (along a left-to-right direction in FIG. 1).

The output shaft (not shown) of the servo motor 112 is connected with an input shaft (not shown) of the reduction gear 113 via a coupling (not shown). An output shaft 113a of the reduction gear 113 is connected with one end of the torque sensor 117. The other end of the torque sensor 117 is connected with one end of the spindle 115. The spindle 115 is rotatably supported by a bearing 114a fixed to a frame 114b of the case 114. To the other end of the spindle 115, fixed is the chuck device 116 for clamping and attaching one end (of one of rotational shafts) of the test body T1 to the first driving unit 110. When the servo motor 112 is driven, the rotation of the output shaft of the servo motor 112 is decelerated by the reduction gear 113, and thereafter transmitted to the one end of the test body T1 via the torque sensor 117, the spindle 115, and the chuck device 116. Further, the spindle 115 has a rotary encoder 115a attached thereto that is configured to detect a rotation angle of the spindle 115.

As shown in FIG. 2, the reduction gear 113 is fixed to the frame 114b of the case 114. Further, the reduction gear 113 includes a gear case (not shown), and a gear mechanism (not shown) rotatably supported by the gear case via a bearing (not shown). Specifically, the case 114 is configured to cover a power transmission shaft extending from the reduction gear 113 to the chuck device 116, and serve as a device frame that rotatably supports the power transmission shaft in positions of the reduction gear 113 and the spindle 115. Namely, the gear mechanism of the reduction gear 113 that is connected with the one end of the torque sensor 117, and the spindle 115 that is connected with the other end of the torque sensor 117 are rotatably supported by the frame 114b of the case via bearings. Therefore, the torque sensor 117 receives a test load (a torsional load) without receiving a bending moment due to weights of the gear mechanism of the reduction gear 113 or the spindle 115 (and chuck device 116). Thus, the torque sensor 117 is allowed to detect the test load with high accuracy.

The plurality of slip rings 119a are formed on a cylindrical surface, on the one-end side, of the torque sensor 117. Meanwhile, a brush holding flame 119c is fixed to the movable plate 111, so as to surround the slip rings 119a from an outer circumferential side of the slip rings 119a. Onto an inner circumference of the brush holding frame 119c, the plurality of brushes 119b are attached, each of which contacts a corresponding one of the slip rings 119a. In a state where the servo motor 112 is driven, and the torque sensor 117 is rotating, the brushes 119b slip on and in contact with the slip rings 119a. The torque sensor 117 is configured to transmit output signals to the slip rings 119a. The output signals from the torque sensor 117 are transmitted via the brushes 119b that contact the slip rings 119a, and are allowed to be received outside the first driving unit 110.

The second driving unit 120 (see FIG. 1) is configured in the same manner as the first driving unit 110. Specifically, in the second driving unit 120, when a servo motor 122 is driven, a chuck device 126 rotates. To the chuck device 126, the other end (one of the rotational shafts) of the test body T1 is fixed. Further, a housing of the test body T1 is fixed to a supporting frame S.

The torsion tester 100 of the first embodiment is configured to apply a torsional load to the test body T1 as a transmission unit for a rear-wheel drive vehicle, by rotating an output shaft O and an input shaft I (on an engine side) in synchronization with each other by the servo motors 112 and 122, respectively, with a difference in a rotational frequency (or in a rotational phase) between the chuck devices 116 and 126, in a state where the output shaft O and the input shaft I are fixed to the chuck device 116 of the first driving unit 110 and the chuck device 126 of the second driving unit 120, respectively. For instance, the torsion tester 100 may be configured to apply a periodically-varying torque to the test body T1, which is the transmission unit for a rear-wheel drive vehicle, by rotating the chuck device 126 of the second driving unit 120 at a constant rotational frequency, and rotating the chuck device 116 of the first driving unit 110 such that a torque detected by the torque sensor 117 varies in accordance with a predetermined waveform.

Thus, the torsion tester 100 of the first embodiment is allowed to precisely drive the input shaft I and the output shaft O of the transmission unit by the servo motors 122 and 112, respectively. Therefore, it is possible to conduct a torsion test under conditions close to actual vehicle traveling conditions, by applying a varying torque to the shafts of the transmission unit while driving the transmission unit.

When a torsion test is conducted for a device with an input shaft I and an output shaft O connected with each other, e.g., via gears as the transmission unit, a torque applied to the input shaft I is not necessarily coincident with a torque applied to the output shaft O. Therefore, in order to more accurately grasp a behavior of the test body T1 in the torsion test, it is preferable to individually measure the torque applied to the input shaft I and the torque applied to the output shaft O. In the first embodiment, as described above, a torque sensor is provided to each of the first driving unit 110 and the second driving unit 120. Hence, it is possible to individually measure the torque applied to the input shaft I and the torque applied to the output shaft O in the transmission unit (the test body T1).

In the aforementioned example, the input shaft I of the transmission unit is driven to rotate at a constant rotational frequency, and a torque is applied to the output shaft O. However, the present invention is not limited to the example. The output shaft O may be driven to rotate at a constant rotational frequency, and a varying torque may be applied to the input shaft I. Alternatively, each of the input shaft I and the output shaft O of the transmission unit may be driven to rotate at a varying rotational frequency. Further, only the torque to be applied to each shaft I and O may be controlled without controlling the rotational frequencies of the shafts. Furthermore, the torques and/or the rotational frequencies for the shafts I and O of the test body T1 may be controlled to vary in accordance with predetermined waveforms. For instance, the torques and/or the rotational frequencies for the shafts I and O of the test body T1 may be controlled to vary in accordance with predetermined waveforms generated by a function generator. Moreover, the torques and/or the rotational frequencies for the shafts I and O of the test body T1 may be controlled to vary according to waveform data of the torques and/or the rotational frequencies that has been acquired in an actual vehicle traveling test.

The torsion tester 100 of the first embodiment is configured such that a distance between the chuck devices 116 and 126 is so adjustable as to meet torsion tests for various transmission units with respective different sizes. Specifically, the movable plate 111 of the first driving unit 110 is configured to be moved relative to the base 110b along a rotational axis direction of the chuck device 116 (along the left-to-right direction in FIG. 1) by a movable-plate driving mechanism (not shown). It is noted that, during the torsion test, the movable plate 111 is firmly fixed to the base 110b by a locking mechanism (not shown). In addition, the second driving unit 120 includes a movable-plate driving mechanism that is substantially the same as the movable-plate driving mechanism of the first driving unit 110.

The torsion tester 100 of the first embodiment according to aspects of the present invention, as described above, is configured to conduct a rotation torsion test for a transmission unit for a rear-wheel drive vehicle. Nonetheless, the present invention is not limited to the configuration described in the first embodiment, but includes a tester for conducting rotation torsion tests for other power transmission mechanisms. The following second, third, and fourth embodiments according to aspects of the present invention will provide examples of torsion testers configured for a transmission unit for a front-wheel drive vehicle, a differential gear unit, and a transmission unit for a four-wheel drive vehicle, respectively.

Second Embodiment

Figure 3:
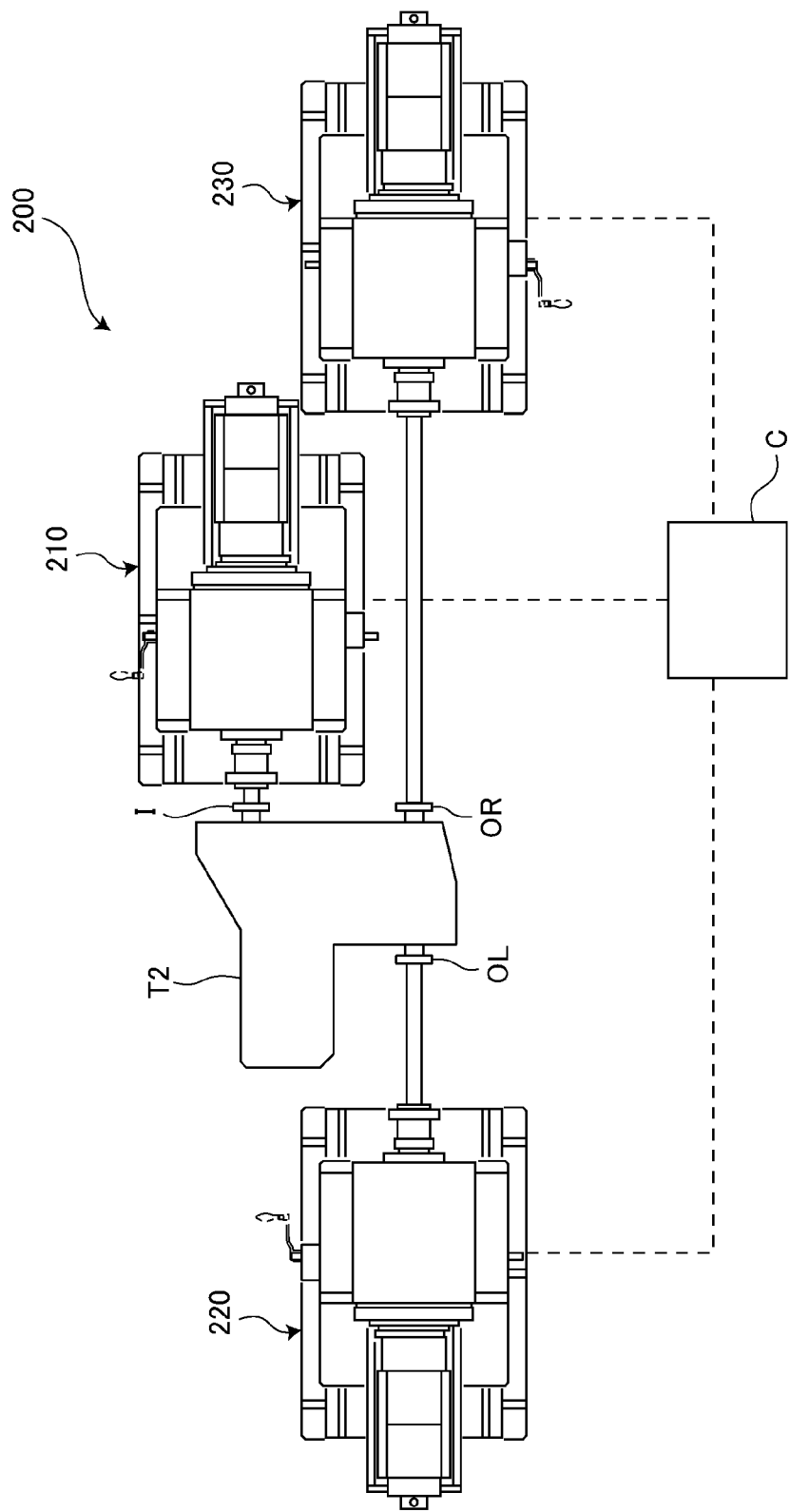
FIG. 3 is a top view of a torsion tester in a second embodiment according to one or more aspects of the present invention.

FIG. 3 is a top view of a torsion tester 200 in a second embodiment according to aspects of the present invention. As described above, the second embodiment provides an example of a torsion tester configured to conduct a torsion test for a transmission unit for a front-wheel drive vehicle as a test body T2. The test body T2, which is a transmission unit including therein a differential gear, includes an input shaft I, a left-side output shaft OL, and a right-side output shaft OR.

The torsion tester 200 of the second embodiment includes a first driving unit 210 configured to drive the input shaft I of the test body T2, a second driving unit 220 configured to drive the left-side output shaft OL, and a third driving unit 230 configured to drive the right-side output shaft OR. Further, the torsion tester 200 includes a controller C configured to take overall control of operations of the torsion tester 200. The first, second, and third driving units 210, 220, and 230 are configured in the same manner as the first driving unit 110 and the second driving unit 120 of the first embodiment. Therefore, explanations will be omitted about specific configurations of the first, second, and third driving units 210, 220, and 230.

When a torsion test is performed for the test body T2 using the torsion tester 200 of the second embodiment, for instance, the input shaft I may be driven to rotate at a predetermined rotational frequency by the first driving unit 210. At the same time, the left-side output shaft OL and the right-side output shaft OR may be driven by the second driving unit 220 and the third driving unit 230, respectively, such that a predetermined torque is applied to each of the left-side output shaft OL and the right-side output shaft OR.

By controlling the first driving unit 210, the second driving unit 220, and the third driving unit 230 as described above, and applying a varying torque to the shafts of the transmission unit while driving the transmission unit, it is possible to conduct a torsion test under conditions close to actual vehicle traveling conditions.

The transmission unit, to be tested using the torsion tester 200 of the second embodiment, is a device in which the input shaft I is connected with the left-side output shaft OL and the right-side output shaft OR via gears. When a torsion test is conducted for the transmission unit, a torque applied to the input shaft I is not coincident with torques applied to the left-side output shaft OL and the right-side output shaft OR. Further, the torque applied to the left-side output shaft OL is not necessarily coincident with the torque applied to the right-side output shaft OR. Therefore, in order to more accurately grasp a behavior of the test body T2 in the torsion test, it is preferable to individually measure the torque applied to the input shaft I, the torque applied to the left-side output shaft OL, and the torque applied to the right-side output shaft OR. In the second embodiment, a torque sensor is provided to each of the first driving unit 210, the second driving unit 220, and the third driving unit 230. Hence, it is possible to individually measure the torque applied to the input shaft I, the torque applied to the left-side output shaft OL, and the torque applied to the right-side output shaft OR in the transmission unit (the test body T2).

It is noted that the second driving unit 220 and the third driving unit 230 may be controlled such that the torque applied to the left-side output shaft OL and the torque applied to the right-side output shaft OR vary in accordance with the same waveform. Further, the second driving unit 220 and the third driving unit 230 may be controlled such that the torque applied to the left-side output shaft OL and the torque applied to the right-side output shaft OR vary in accordance with respective different waveforms (e.g., with mutually opposite phases).

Further, each of the left-side output shaft OL and the right-side output shaft OR may be driven to rotate at a constant rotational frequency, and the input shaft I may be driven to rotate at a periodically-varying rotational frequency. Alternatively, the input shaft I, the left-side output shaft OL, and the right-side output shaft OR may be driven to rotate at individually-varying rotational frequencies, respectively.

Third Embodiment

Figure 4:
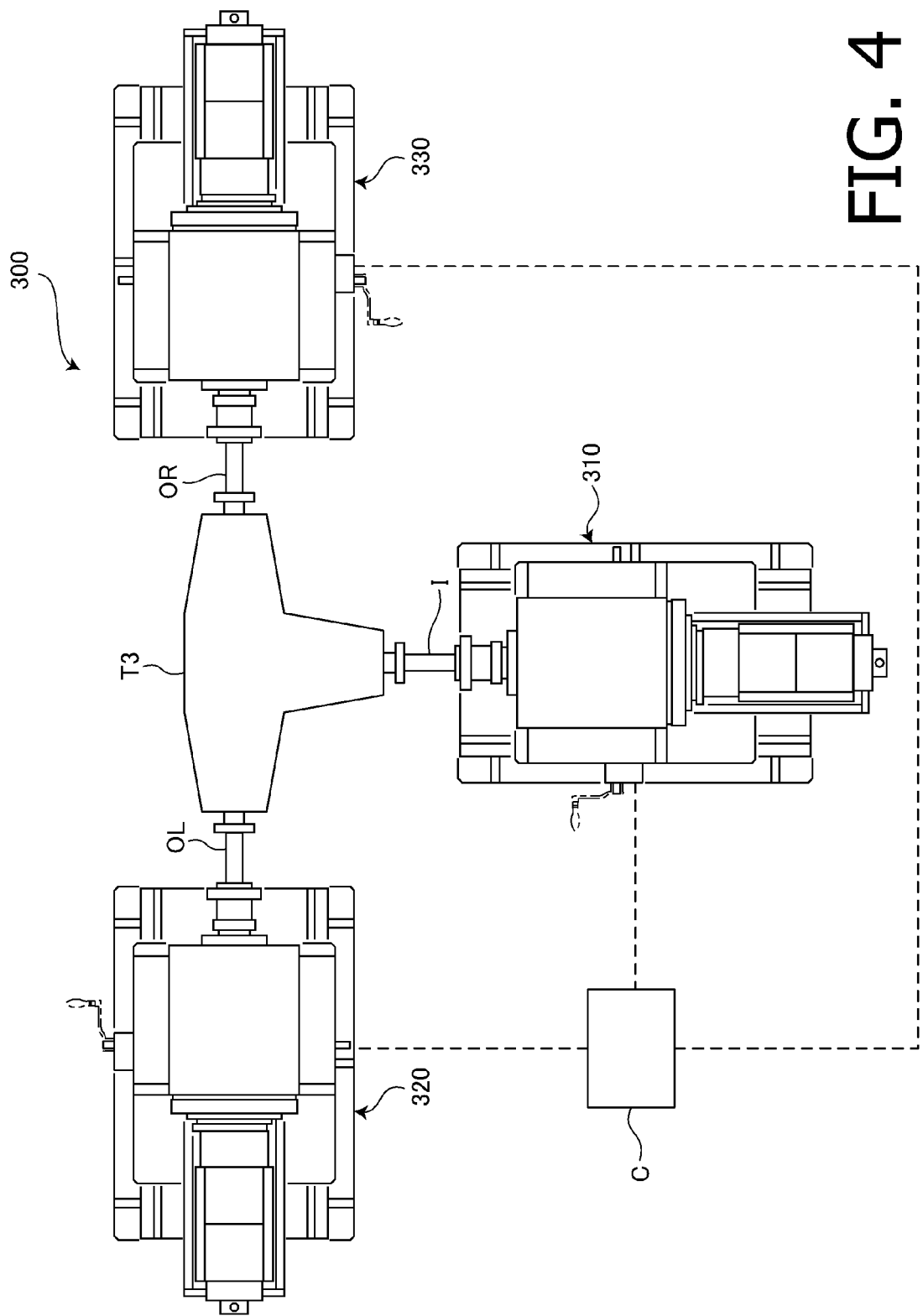
FIG. 4 is a top view of a torsion tester in a third embodiment according to one or more aspects of the present invention.

Next, a third embodiment according to aspects of the present invention will be described. FIG. 4 is a top view of a torsion tester 300 in the third embodiment according to aspects of the present invention. The third embodiment provides an example of a torsion tester configured to conduct a torsion test for a differential gear unit for a rear-wheel drive vehicle as a test body T3. In the same manner as the second embodiment, the test body T3 includes an input shaft I, a left-side output shaft OL, and a right-side output shaft OR.

The torsion tester 300 of the third embodiment includes a first driving unit 310 configured to drive the input shaft I of the test body T3, a second driving unit 320 configured to drive the left-side output shaft OL, and a third driving unit 330 configured to drive the right-side output shaft OR. Further, the torsion tester 300 includes a controller C configured to take overall control of operations of the torsion tester 300. The first, second, and third driving units 310, 320, and 330 are configured in the same manner as the first driving unit 110 and the second driving unit 120 of the first embodiment. Therefore, explanations will be omitted about specific configurations of the first, second, and third driving units 310, 320, and 330.

When a torsion test is performed for the test body T3 using the torsion tester 300 of the third embodiment, for instance, the input shaft I may be driven to rotate at a predetermined rotational frequency by the first driving unit 310. At the same time, the left-side output shaft OL and the right-side output shaft OR may be driven by the second driving unit 320 and the third driving unit 330, respectively, such that a predetermined torque is applied to each of the left-side output shaft OL and the right-side output shaft OR.

By controlling the first driving unit 310, the second driving unit 320, and the third driving unit 330 as described above, and applying a varying torque to the shafts of the test body T3 while driving each shaft of the test body T3, it is possible to conduct a torsion test under conditions close to actual vehicle traveling conditions.

In the same manner as the transmission unit, the differential gear unit is a device in which the input shaft I is connected with the left-side output shaft OL and the right-side output shaft OR via gears. When a torsion test is conducted for the differential gear unit, a torque applied to the input shaft I is not coincident with torques applied to the left-side output shaft OL and the right-side output shaft OR. Further, the torque applied to the left-side output shaft OL is not necessarily coincident with the torque applied to the right-side output shaft OR. Therefore, in order to more accurately grasp a behavior of the test body T3 in the torsion test, it is preferable to individually measure the torque applied to the input shaft I, the torque applied to the left-side output shaft OL, and the torque applied to the right-side output shaft OR. In the third embodiment, a torque sensor is provided to each of the first driving unit 310, the second driving unit 320, and the third driving unit 330. Hence, it is possible to individually measure the torque applied to the input shaft I, the torque applied to the left-side output shaft OL, and the torque applied to the right-side output shaft OR in the differential gear unit (the test body T3).

It is noted that the second driving unit 320 and the third driving unit 330 may be controlled such that a rotational frequency of the left-side output shaft OL and a rotational frequency of the right-side output shaft OR vary according to the same waveform. Further, the second driving unit 320 and the third driving unit 330 may be controlled such that the rotational frequency of the left-side output shaft OL and the rotational frequency of the right-side output shaft OR vary in accordance with respective different waveforms (e.g., such waveforms that a rotational frequency difference between the input shaft I and the left-side output shaft OL and a rotational frequency difference between the input shaft I and the right-side output shaft OR vary with mutually opposite phases).

Further, each of the left-side output shaft OL and the right-side output shaft OR may be driven to rotate at a constant rotational frequency, and the input shaft I may be driven to rotate at a periodically-varying rotational frequency. Alternatively, each of the input shaft I, the left-side output shaft OL, and the right-side output shaft OR may be driven to rotate at a varying rotational frequency.

Fourth Embodiment

Figure 5:
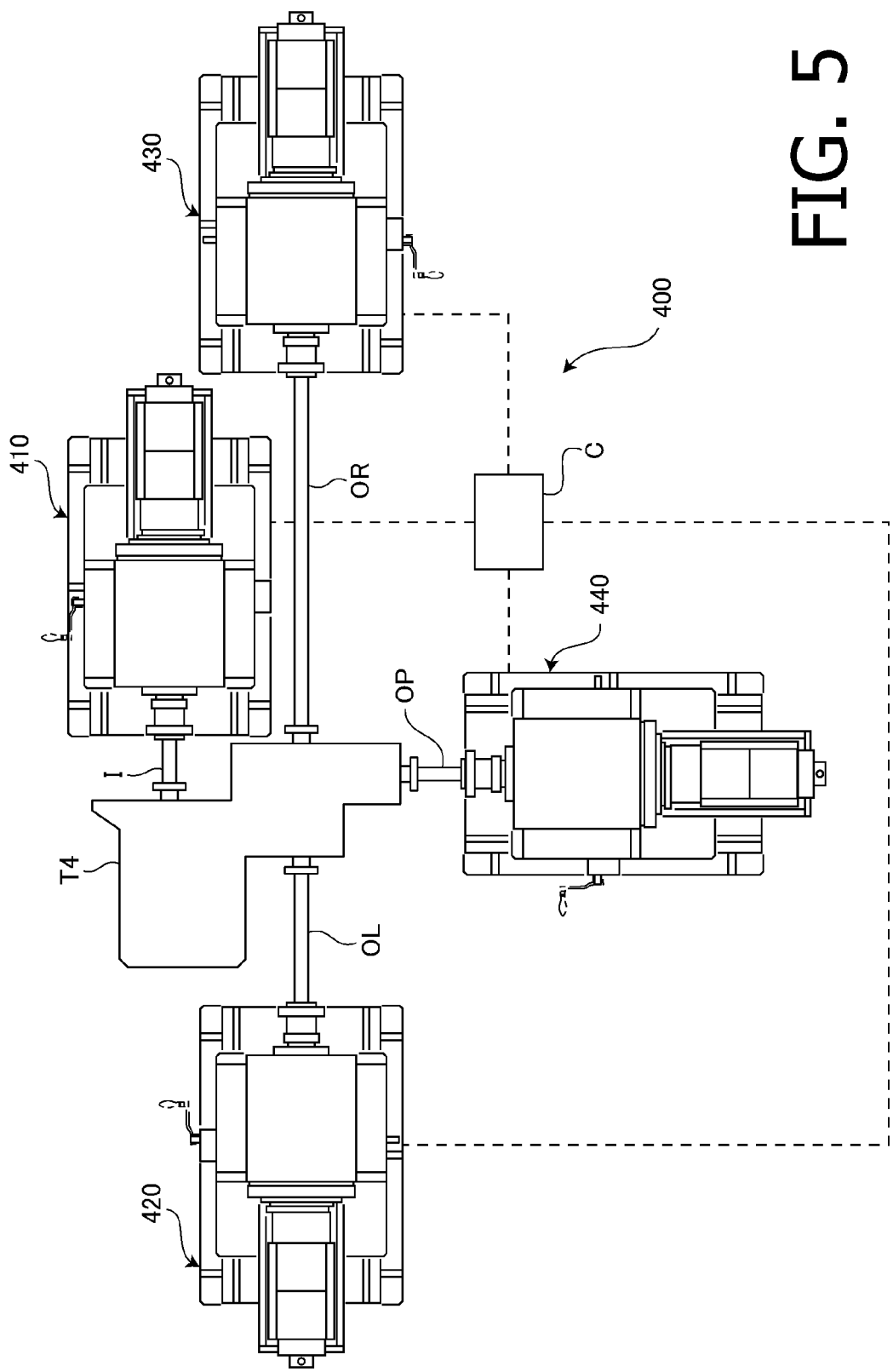
FIG. 5 is a top view of a torsion tester in a fourth embodiment according to one or more aspects of the present invention.

FIG. 5 is a top view of a torsion tester 400 in a fourth embodiment according to aspects of the present invention. The torsion tester 400 of the fourth embodiment is an example of torsion testers configured to conduct a rotation torsion test for a test body T4 having four rotational shafts. Hereinafter, an explanation will be provided about an example case where a rotation torsion test is performed for a four-wheel drive system (4WD system) as the test body T4. The test body T4 is a front-wheel-drive-based electronically controlled 4WD system, which includes a transmission (not shown), a front differential gear (not shown), a transfer (not shown), and an electronically controlled multiple disk clutch (not shown). The test body T4 includes an input shaft I configured to be connected with an engine, a left-side output shaft OL configured to be connected with a drive shaft for a left front wheel, a right-side output shaft OR configured to be connected with a drive shaft for a right front wheel, and a rear output shaft OP configured to be connected with a propeller shaft for transmitting a power to rear wheels. A driving force transmitted from the input shaft I to the test body T4, after decelerated by the transmission provided to the test body T4, is distributed to the left-side output shaft OL and the right-side output shaft OR via the front differential gear. Further, a part of the driving force transmitted to the front differential gear is branched to the transfer, and is output from the rear output shaft OP.

The torsion tester 400 of the fourth embodiment includes a first driving unit 410 configured to drive the input shaft I of the test body T4, a second driving unit 420 configured to drive the left-side output shaft OL, a third driving unit 430 configured to drive the right-side output shaft OR, and a fourth driving unit 430 configured to drive the rear output shaft OP. Further, the torsion tester 400 includes a controller C configured to take overall control of operations of the torsion tester 400. The first, second, third, and fourth driving units 410, 420, 430, and 440 are configured in the same manner as the first driving unit 110 and the second driving unit 120 of the first embodiment. Therefore, explanations will be omitted about specific configurations of the first, second, third, and fourth driving units 410, 420, 430, and 440.

Subsequently, an explanation will be provided about an example of control to be taken in a rotation torsion test for the test body T4 using the torsion tester 400. As described above, the test body T4 includes the front differential gear (not shown), and is configured to cause a rotational frequency difference between the left-side output shaft OL and the right-side output shaft OR based on a difference between a torque applied to the left-side output shaft OL and a torque applied to the right-side output shaft OR. The following rotation torsion test is conducted for the test body T4 in a state where the front differential gear of the test body T4 is driven such that the left-side output shaft OL rotates at a rotational frequency different from a rotational frequency of the right-side output shaft OR. Specifically, in the rotation torsion test, performance of the test body T4 is evaluated by driving the left-side output shaft OL and the right-side output shaft OR with a rotational frequency difference therebetween while rotating the input shaft I at a constant rotational frequency (at a constant number of revolutions per minute). Further, in the following rotation torsion test of the fourth embodiment, taken is such control as to keep constant a sum of the torque applied to the left-side output shaft OL and the torque applied to the right-side output shaft OR.

Figure 6:
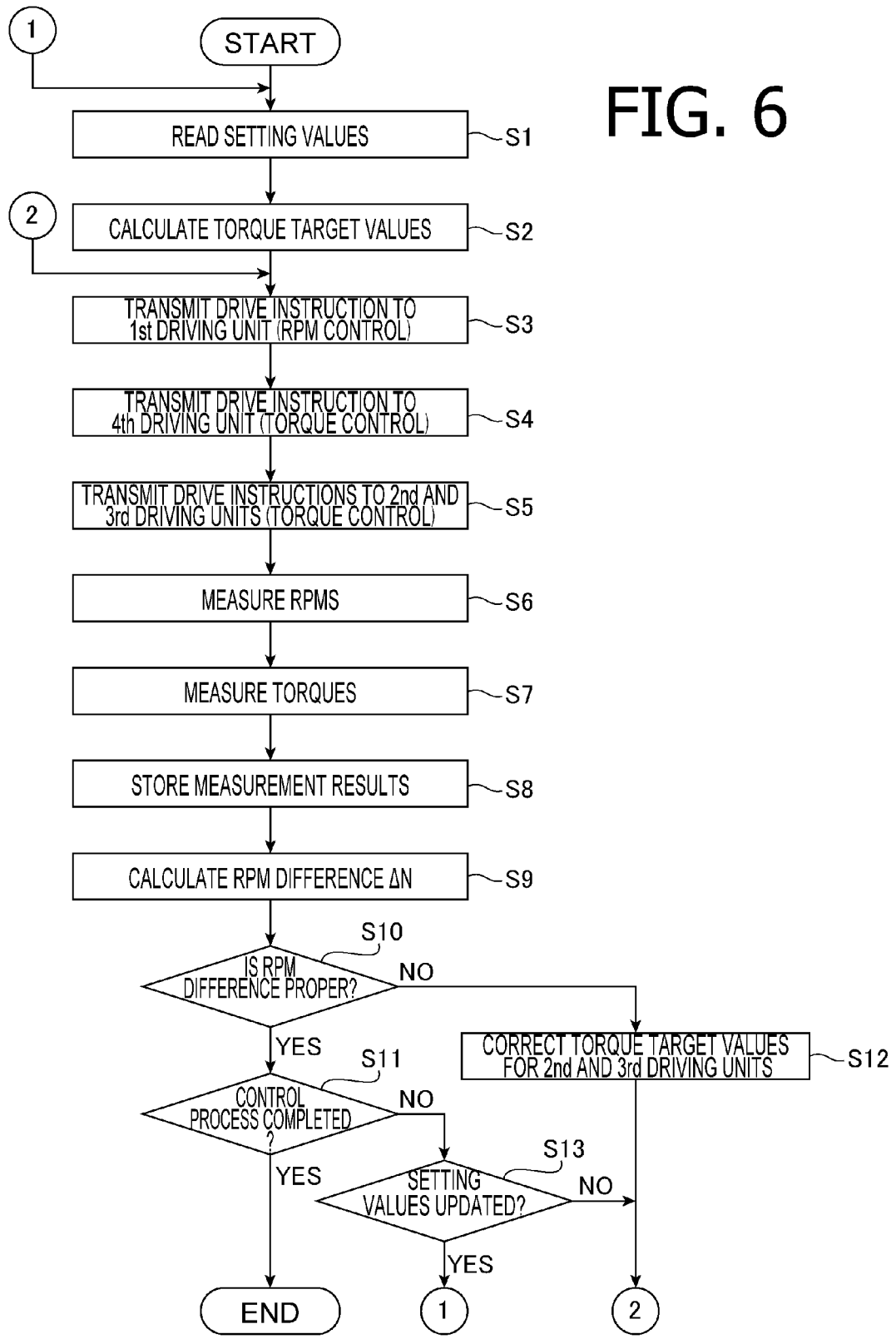
FIG. 6 is a flowchart showing a procedure of a control process for a rotation torsion test using the torsion tester in the fourth embodiment according to one or more aspects of the present invention.

FIG. 6 is a flowchart showing a procedure of a control process for a rotation torsion test using the torsion tester 400. In the fourth embodiment, the rotation torsion test is conducted by rotating the left-side output shaft OL and the right-side output shaft OR with a predetermined rotational frequency difference therebetween while driving the input shaft I at a constant rotational frequency, and applying torque loads to the left-side output shaft OL and the right-side output shaft OR so as to keep constant the sum of the torque applied to the left-side output shaft OL and the torque applied to the right-side output shaft OR. It is noted that the control process shown in FIG. 6 is carried out by the controller C.

In the control process for the torsion tester 400 shown in FIG. 6, first, the controller C reads out, from a storage device (not shown), various setting values (test conditions) previously set (S1). For instance, the setting values include the number of revolutions per minute N1 (hereinafter referred to as the RPM N1) of the first driving unit 410 (the input shaft I), an RPM difference ($\Delta N=N2-N3$) between an RPM N2 of the second driving unit 420 (the left-side output shaft OL) and an RPM N3 of the third driving unit 430 (the right-side output shaft OR), and a sum (Tm2+Tm3) of a torque Tm2 applied to the left-side output shaft OL and a torque Tm3 applied to the right-side output shaft OR, and a torque Tm4 applied to the rear output shaft OP by the fourth driving unit 440. Table 1 shows an example of the setting values read in S1.

TABLE 1

| Setting Parameters | Setting Values |
|---|---|
| N1 | 50 [rpm] |
| ΔN (= N2 − N3) | 2 [rpm] |
| Tm2 + Tm3 | 10000 [N · m] |
| Tm4 | 1000 [N · m] |

In the fourth embodiment, for the first driving unit 410, RPM control is taken with the RPM as a control parameter. Meanwhile, for the second driving unit 420, the third driving unit 430, and the fourth driving unit 440, torque control is taken with the torque as a control parameter. In general, for the second driving unit 420 and the third driving unit 430, the RPM control is applied since the RPM difference between the second driving unit 420 and the third driving unit 430 needs to be controlled. However, the inventors of the present invention have acquired the following findings through their researches. An operation of the front differential gear (not shown) incorporated in the test body T4 rapidly changes due to a slight difference between the torque applied to left-side output shaft OL and the right-side output shaft OR. Hence, in the RPM control with a great delay in the control (more directly, a great delay in detection of control values), it is impossible to reproduce, with high accuracy, loads applied to the test body T4 when the test body T4 is actually mounted on an automobile. In view of the problem, in the fourth embodiment, for the second driving unit 420 and the third driving unit 430, taken is the torque control in which the controller C calculates target values of the torques to be applied to the left-side output shaft OL and the right-side output shaft OR, based on the setting value of the RPM difference between the left-side output shaft OL and the right-side output shaft OR.

After reading the setting values (S1), the controller C calculates target values in the torque control of the left-side output shaft OL and the right-side output shaft OR (S2). Specifically, in S2, initially, the controller C calculates predicted values of the RPM N2 of the second driving unit 420 and the RPM N3 of the third driving unit 430.

A transmission gear ratio r of the front wheels of the test body T4 is represented by the following expression 1.

$$r = \frac{\left(\frac{N_2 + N_3}{2}\right)}{N1},$$ [Expression 1]

where
N1 represents the RPM (the number of revolutions per minute) of the input shaft I,
N2 represents the RPM of the left-side output shaft OL, and
N3 represents the RPM of the right-side output shaft OR.

The expression 1 is transformed into the following expression 2.

$$N2+N3=2\cdot r\cdot N1$$ [Expression 2]

Further, from the definition of the RPM difference ΔN, the following expression 3 is obtained.

$$N2-N3=\Delta N$$ [Expression 3]

The RPM N2 and the RPM N3 are represented by the following expressions 4 and 5 as solutions of simultaneous equations of the expressions 2 and 3, respectively.

$$N2 = r\cdot N1 + \frac{\Delta N}{2}$$ [Expression 4]

$$N3 = r\cdot N1 - \frac{\Delta N}{2}$$ [Expression 5]

The RPM N2 of the second driving unit 420 and the RPM N3 of the third driving unit 430 are calculated by substituting, into the expressions 4 and 5, the RPM N1 and the RPM difference ΔN acquired in S1 (see Table 1), and a known transmission gear ratio r=0.1, respectively. In the fourth embodiment, N2=6 rpm, and N3=4 rpm.

Subsequently, the controller C calculates initial values of the target values of the torque Tm2 of the second driving unit 420 and the torque Tm3 of the third driving unit 430. In the fourth embodiment, in order to keep the RPM difference ΔN constant, it is required to set the torques Tm2 and Tm3 to the same target value. Accordingly, the target values of the torques Tm2 and Tm3 are calculated using the following expression 6.

$$Tm2 = Tm3 = \frac{Tm2 + Tm3}{2}$$ [Expression 6]

Next, the controller C transmits, to the first driving unit 410, a drive instruction containing the target value of the RPM N1 (S3).

Next, the controller C transmits, to the fourth driving unit 440, a drive instruction containing the target value of the torque Tm4 (S4).

Next, the controller C transmits, to the second driving unit 420, a drive instruction containing the target value of the torque Tm2, and transmits, to the third driving unit 430, a drive instruction containing the target value of the torque Tm3 (S5).

Next, the controller C measures the RPM N1 (unit: rpm) of the first driving unit 410, the RPM N2 (unit: rpm) of the second driving unit 420, the RPM N3 (unit: rpm) of the third driving unit 430, and the RPM N4 (unit: rpm) of the fourth driving unit 440, based on signals from rotary encoders (each identical to the rotary encoder 115*a* in FIG. 2) provided to the first driving unit 410, the second driving unit 420, the third driving unit 430, and the fourth driving unit 440, respectively (S6).

Next, the controller C measures the torque Tm1 (unit: N·m) of the first driving unit 410, the torque Tm2 (unit: N·m) of the second driving unit 420, the torque Tm3 (unit: N·m) of the third driving unit 430, and the torque Tm4 (unit: N·m) (unit: rpm) of the fourth driving unit 440, based on signals from the torque sensors 117 provided to the first driving unit 410, the second driving unit 420, the third driving unit 430, and the fourth driving unit 440, respectively (S7).

Next, the controller C stores, into a memory incorporated therein, the RPMs N1, N2, N3, and N4 measured in S6 and the torques Tm1, Tm2, Tm3, and Tm4 measured in S7 (S8).

Next, the controller C determines (calculates) the RPM difference ΔN=N2−N3, from the RPM N2 and the RPM N3 measured in S6 (S9). Then, the controller C determines whether the RPM difference ΔN calculated in S9 is proper (S10). Specifically, the controller C determines that the RPM difference ΔN is not properly controlled (S10: No), when comparing the RPM difference ΔN calculated in S9 with the setting value previously set for the RPM difference ΔN (see Table 1), and determining that a difference between the calculated RPM difference ΔN and the previously set RPM difference ΔN is beyond a predetermined range. In this case, the controller C corrects the target value of the torque Tm2 of the second driving unit 420 and the target value of the torque Tm3 of the third driving unit 430 (S12). Thereafter, the controller C goes back to S3, and then transmits a drive instruction to the driving unit 410 (S3), transmits a drive instruction to the driving unit 440 (S4), and transmits drive instructions to the driving units 420 and 430 (S5).

In S12, the controller C corrects the target value of the torque Tm2 by adding a correction value a to the torque Tm2 in accordance with the following expression 7. Further, the controller C corrects the target value of the torque Tm3 by subtracting the correction value a from the torque Tm3 in accordance with the following expression 8.

$$Tm2 \leftarrow Tm2 + \alpha \qquad [\text{Expression 7}]$$

$$Tm3 \leftarrow Tm3 - \alpha \qquad [\text{Expression 8}]$$

Further, the correction value a is calculated in accordance with the following expression 9.

$$\alpha = \frac{Tm2 + Tm3}{2} \cdot \frac{\frac{\Delta N_{set} - \Delta N_{meas}}{2}}{\frac{N2 + N3}{2}} \qquad [\text{Expression 9}]$$

When determining that the difference between the calculated RPM difference ΔN and the previously set RPM difference ΔN is within the predetermined range, the controller C determines that the RPM difference ΔN is properly controlled (S10: Yes). When determining that the controller C does not terminate, but will continue the control process for the torsion tester 400 (S11: No), the controller C verifies whether the setting values (see Table 1) have been updated (S13). When determining that the setting values have not been updated (S13: Yes), the controller C goes back to S1, and again reads out the setting values. Meanwhile, when determining that the setting values have been updated (S13: No), the controller C goes back to S3, and then transmits a drive instruction to the driving unit 410 (S3), transmits a drive instruction to the driving unit 440 (S4), and transmits drive instructions to the driving units 420 and 430 (S5).

By controlling the first driving unit 410, the second driving unit 420, the third driving unit 430, and the fourth driving unit 440 as described above, it is possible to conduct the rotation torsion test for the test body T4 in a state where the RPM difference is provided between the left-side output shaft OL and the right-side output shaft OR.

In the fourth embodiment, the torque control is taken of the second driving unit 420 and the third driving unit 430 under such conditions as to keep constant the RPM difference ΔN between the second driving unit 420 (the left-side output shaft OL) and the third driving unit 430 (the right-side output shaft OR), and to keep constant the sum (Tm2+Tm3) of the torque Tm2 of the second driving unit 420 (the left-side output shaft OL) and the torque Tm3 of the third driving unit 430 (the right-side output shaft OR). Nonetheless, a control method according to aspects of the present invention is not limited to the aforementioned control method. For instance, the control method may be configured to apply previously set static or dynamic torques Tm2 and Tm3 to the second driving unit 420 and the third driving unit 430, respectively, without setting any condition regarding the RPM difference ΔN. Further, the control method may be configured to take RPM control of the second driving unit 420 and the third driving unit 430 so as to maintain the RPM difference ΔN, without setting any condition for keeping constant the sum (Tm2+Tm3) of the torque Tm2 of the second driving unit 420 (the left-side output shaft OL) and the torque Tm3 of the third driving unit 430 (the right-side output shaft OR).

Further, in the fourth embodiment, the first driving unit 410 is driven to rotate at a constant rotational frequency (at a constant RPM). Nonetheless, the rotation torsion test may be conducted by varying the RPM of the first driving unit 410, e.g., according to a predetermined waveform. For instance, the second driving unit 420 and the third driving unit 430 may be controlled to vary the RPM of the left-side output shaft OL and the RPM of the right-side output shaft OR in accordance with the same waveform. Further, the second driving unit 420 and the third driving unit 430 may be controlled to vary the RPM of the left-side output shaft OL and the RPM of the right-side output shaft OR in accordance with respective different waveforms (e.g., such waveforms that a rotational frequency difference between the input shaft I and the left-side output shaft OL and a rotational frequency difference between the input shaft I and the right-side output shaft OR vary with mutually opposite phases).

Further, in the fourth embodiment, the fourth driving unit 440 is driven by a constant torque. Nonetheless, the rotation torsion test may be conducted by varying the torque of the fourth driving unit 440, e.g., according to a predetermined waveform. Further, in the fourth embodiment, taken is such control as to keep constant the RPM difference between the left-side output shaft OL and the right-side output shaft OR. Nonetheless, the rotation torsion test may be conducted by varying the RPM difference between the left-side output shaft OL and the right-side output shaft OR, e.g., according to a predetermined waveform.

The test body T4 of the fourth embodiment is configured such that the input shaft I, the left-side output shaft OL, the right-side output shaft OR, and the rear output shaft OP are connected with each other via gears. Hence, the torques applied to the input shaft I, the left-side output shaft OL, the right-side output shaft OR, and the rear output shaft OP are not coincident with each other. Therefore, in order to more accurately grasp a behavior of the test body T4 in the torsion test, it is preferable to individually measure the torque applied to the input shaft I, the torque applied to the left-side output shaft OL, the torque applied to the right-side output shaft OR, and the torque applied to the rear output shaft OP. In the fourth embodiment, a torque sensor is provided to each of the first driving unit 410, the second driving unit 420, the third driving unit 430, and the fourth driving unit 440. Hence, it is possible to individually measure the torque applied to the input shaft I, the torque applied to the left-side output shaft OL, the torque applied to the right-side output shaft OR, and the torque applied to the rear output shaft OP in the test body T4.

Further, each of the left-side output shaft OL, the right-side output shaft OR, and the rear output shaft OP may be driven to rotate at a constant rotational frequency (at a constant RPM), and the input shaft I may be driven to rotate at a periodically-varying rotational frequency. Alternatively, each of the input shaft I, the left-side output shaft OL, the right-side output shaft OR, and the rear output shaft OP may be driven to rotate at a varying rotational frequency (at a varying RPM).

Further, each of the aforementioned embodiments provides an example in which the rotation torsion test is conducted. Nonetheless, one of the driving units may be controlled to serve as a reaction-force portion without being rotated, so as to conduct regular torsion tests using the torsion testers 100, 200, 300, and 400.

Hereinabove, the embodiments according to aspects of the present invention have been described. The present invention can be practiced by employing conventional materials, methodology and equipment. Accordingly, the details of such materials, equipment and methodology are not set forth herein in detail. In the previous descriptions, numerous specific details are set forth (such as specific materials, structures, chemicals, processes, etc.) in order to provide a thorough understanding of the present invention. However, it should be recognized that the present invention can be practiced without reapportioning to the details specifically set forth. In other instances, well known processing structures have not been described in detail, in order not to unnecessarily obscure the present invention.

Only exemplary embodiments of the present invention and but a few examples of their versatility are shown and described in the present disclosure. It is to be understood that the present invention is capable of use in various other combinations and environments and is capable of changes or modifications within the scope of the inventive concept as expressed herein. For example, the following modifications are possible. It is noted that, in the following modifications, explanations of the same configurations as exemplified in the aforementioned embodiments will be omitted.

What is claimed is:

1. A torsion tester comprising:
   three or more driving units each of the driving units being configured to connect with and rotate a corresponding one of three or more input/output shafts of a test body, respectively; and
   a controller configured to individually control each of the three or more driving units to be driven with one of individually-set rotational frequencies and individually-set torques, respectively, each of the three or more driving units being controllable with an individually-varying rotational frequency during a test,
   wherein the three or more driving units comprise:
   a first driving unit configured to connect with an input shaft of the test body; and
   two second driving units configured to connect with output shafts of the test body, and
   wherein the controller is configured to:
   record a setting value of a rotational frequency difference between the two second driving units and a setting value of a sum of the torques to be applied to the two second driving units; and
   set respective torques to be applied to the output shafts of the test body based on the recorded frequency difference while keeping constant the sum of the torques to be applied to the two second driving units.

2. The torsion tester according to claim 1,
   wherein the three or more driving units comprise a plurality of the first driving units, and
   wherein the controller is configured to drive the plurality of first driving units with one of individually-set torques and individually-set rotational frequencies, respectively.

3. The torsion tester according to claim 2,
   wherein each of the three or more driving units comprises:
   a drive shaft configured to connect with one of an input shaft and an output shaft of the test body;
   a rotation detector configured to detect a rotational frequency of the drive shaft; and
   a torque sensor configured to detect a torque applied to the drive shaft.

4. The torsion tester according to claim 2,
   wherein each of the three or more driving units comprises:
   a servo motor;
   a reduction gear configured to reduce a rotational speed of an output shaft of the servo motor; and
   a chuck configured to clamp one of an input shaft and an output shaft of the test body, and transmit an output force from the reduction gear to the one of the input shaft and the output shaft of the test body, and
   wherein the torque sensor is configured to transmit the output force from the reduction gear to the chuck.

5. The torsion tester according to claim 4,
   wherein each of the three or more driving units comprises:
   a spindle configured to connect the torque sensor with the chuck; and
   a bearing configured to rotatably support the spindle, and
   wherein a power transmission shaft extending from the reduction gear to the chuck is rotatably supported by the reduction gear and the bearing.

6. The torsion tester according to claim 4,
   wherein each of the three or more driving units comprises:
   a slip ring attached between the output shaft of the reduction gear and the chuck; and
   a brush formed to surround the slip ring from an outer circumferential side of the slip ring, the brush configured to slip on the slip ring while contacting the slip ring when the servo motor is driven, and
   wherein each of the three or more driving units is configured to transmit an output signal from the torque sensor to the brush via the slip ring.

7. The torsion tester according to claim 1,
   wherein the controller is further configured to provide:
   a rotational frequency difference determiner configured to determine a measurement-based value of the rotational frequency difference between the plurality of second driving units, based on detection results of rotational frequencies detected by the rotation detectors of the plurality of second driving units; and
   a torque corrector configured to correct respective setting values of the torques to be applied to the plurality of output shafts of the test body, based on:
   the setting value, of the rotational frequency difference between the plurality of second driving units; and
   the measurement-based value, determined by the rotational frequency difference determiner, of the rotational frequency difference between the plurality of second driving units.

8. The torsion tester according to claim 1,
   wherein the three or more driving units are configured in a same manner.

9. A torsion tester comprising:
   three or more driving units each of the driving units being configured to connect with and rotate a corresponding one of three or more input/output shafts of a test body, respectively, each driving unit comprising:
   a drive shaft configured to connect with one of an input shaft and an output shaft of the test body;

a rotation detector configured to detect a rotational frequency of the drive shaft; and a torque sensor configured to detect a torque applied to the drive shaft; and a controller configured to individually control each of the three or more driving units to be driven with one of individually-set rotational frequencies and individually-set torques, respectively, each of the three or more diving units being controllable with an individually-varying rotational frequency during a test, wherein the three or more driving units comprise:

a first driving unit configured to connect with an input shaft of the test body; and two second driving units configured to connect with output shafts of the test body, and wherein the controller is configured to:

record a setting value of a rotational frequency difference between the two second driving units and a setting value of a sum of the torques to be applied to the two second driving units; and set respective torques to be applied to the output shafts of the test body based on the recorded frequency difference while keeping constant the sum of the torques to be applied to the two second driving units.

* * * * *